United States Patent [19]
Teng

[11] Patent Number: 5,241,084
[45] Date of Patent: Aug. 31, 1993

[54] PREPARATION PROCESS OF GINKGOLIDE B FROM GINKGOLIDE C

[75] Inventor: Beng-Poon Teng, Villeneuve Les Avignon, France

[73] Assignee: Societe de Conseils de Recherches et d'Applications Scientifiques (S.C.R.A.S.), France

[21] Appl. No.: 860,165

[22] Filed: Mar. 30, 1992

[30] Foreign Application Priority Data

Apr. 9, 1991 [GB] United Kingdom ................ 9107425

[51] Int. Cl.$^5$ .......................................... C07D 307/77
[52] U.S. Cl. .......................................... 549/297
[58] Field of Search .......................................... 549/297

[56] References Cited

U.S. PATENT DOCUMENTS 4,734,280  3/1988  Braquet ........................ 424/195.1
5,089,636  2/1992  Kwak et al. ........................ 549/297

OTHER PUBLICATIONS

Weinges, K. et al. "Isolierung und Strukturaufklärung eines neuen Ginkgolids" Liebigs Ann Chem (1987) 521-526.
J. Chem. Soc. C, 1967, vol. (21), pp. 2201-2206, see momoacetate of Ginkgolide B, p. 2205, LH column.
K. Weinges et al., "Herstellung von Ginkgolid B aus Ginkgolid C", Liebigs Annalen Der Chemie, No. 1, Jan. 1991, pp. 81-83.

Primary Examiner—Warren C. Ivy
Assistant Examiner—A. A. Owens
Attorney, Agent, or Firm—Lucas & Just

[57] ABSTRACT

The invention relates to a process for the preparation of ginkgolide B from ginkgolide C and to ginkgolide B thus obtained, the process comprising the following succession of four steps:

protecting the 10-hydroxy group of ginkgolide C by conversion to an alkyl ester, the reaction being effected in dimethylformamide at a temperature of from 15° to 50° C. for from 4 to 10 hours;

activating the 7-hydroxy group of the resultant 10-protected ginkgolide C by conversion to a (R)thiocarbonyl ester, the activation being effected in basic conditions at a temperature of from 0° to 40° C. for from 1 to 24 hours;

deoxygenating the 7-activated group in the resultant 10-protected 7-activated ginkgolide C by treating it with tributyltin hydride or tris-(trimethylsilyl)silane, in an aprotic solvent, in the presence of a free-radical generator, the reaction being effected at a temperature of from 70° to 110° C. for from 15 minutes to 3 hours under inert atmosphere, and cleaving the protecting group from the 10-hydroxy group of the resultant 10-protected ginkgolide B.

9 Claims, No Drawings

PREPARATION PROCESS OF GINKGOLIDE B FROM GINKGOLIDE C

The invention relates to a process for the preparation of ginkgolide B from ginkgolide C and to ginkgolide B thus obtained.

Ginkgolides B and C are diterpene lactones which are isolated from leaves and roots of the ginkgo biloba tree in generally comparable proportions (the proportions vary according to the material and to the source of the same and also to the extraction method used). Ginkgolide B has been found to be a potent inhibitor of PAF-acether (cf for instance U.S. Pat. No. 4,734,280) whereas ginkgolide C is less active in this regard. As ginkgolides are extracted in generally comparable proportions, it was interesting to convert ginkgolide C into ginkgolide B, insofar that starting from a less costly product renders the conversion process definitely cheaper than the extraction.

The invention provides a process for the preparation of ginkgolide B, of the formula B

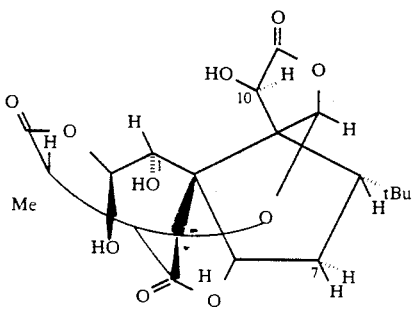

from ginkgolide C, of the formula C

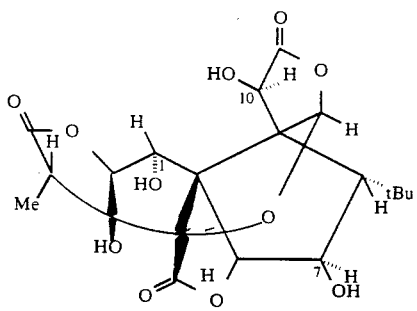

the process comprising the following succession of four steps:

protecting the 10-hydroxy group of ginkgolide C by conversion to an alkyl ester, the reaction being effected in dimethylformamide at a temperature of from 15° to 50° C. for from 4 to 10 hours;

activating the 7-hydroxy group of the resultant 10-protected ginkgolide C by conversion to a (R)thiocarbonyl ester wherein R represents a phenoxy group, a phenoxy group substituted by one or several halogen atom(s), or the imidazolyl group, by treating it respectively with an activating agent selected from within a phenylthiocarbonate, the phenyl group being optionally substituted by one or several halogen atom(s), and 1,1'-thiocarbonyldiimidazole, the activation being effected in basic conditions at a temperature of from 0° to 40° C. for from 1 to 24 hours;

deoxygenating the 7-activated group of the resultant 10-protected 7-activated ginkgolide C by treating it with tributyltin hydride or tris-(trimethylsilyl)silane, in an aprotic solvent, in the presence of a free-radical generator, the reaction being effected at a temperature of from 70° to 110° C. for from 15 minutes to 3 hours under inert atmosphere, and cleaving the protecting group for getting the 10-hydroxy group from the hereabove 10-protected ginkgolide B.

In the first step, the C-10 hydroxy group of ginkgolide C can be preferably protected as an acetyl, n-butyryl or n-valeryl ester and the protecting agent for such conversion being respectively acetic anhydride, n-butyric anhydride and n-valeric anhydride. Preferably, the reaction is carried out at a temperature of from 20° to 40° C. for from 7 to 9 hours.

The second step in the process of the invention is the activation of the 7-hydroxy group of ginkgolide C. The said 7-hydroxy group is converted to a (R)thiocarbonyl ester wherein R represents preferably the phenoxy, 2,4,6-trichlorophenoxy, pentafluorophenoxy or imidazolyl group, by treating it with 1 to 3 equivalents of an activating agent selected from within phenylchlorothionoformate, 2,4,6-trichlorophenylchlorothionoformate, pentafluorophenylchlorothionoformate and 1,1'-thiocarbonyldiimidazole respectively. The reaction is preferably carried out in solvents mixture containing at least pyridine (1 to 90% by volume) or in acetonitrile containing 2 to 4 equivalents of 4-(dimethylamino)pyridine.

In the third step, the deoxygenation of the 7-activated group is preferably carried out in suitable solvent selected from within acetonitrile, benzene, toluene or mixtures thereof, in the presence of a free-radical generator selected from within $\alpha,\alpha'$-azoisobutyronitrile and ter-butylhydroperoxide. 2 to 4 equivalents of tributyltin hydride or tris-(trimethylsilyl)silane in suitable solvents can be used in proportions wherein the derivative is soluble in the presence of 0.01 to 0.1 equivalent of the free-radical generator. The inert atmosphere may consist of nitrogen or argon atmosphere.

In the fourth step of the process of the invention, the cleavage of the 10-protecting group may be effected by any conventional method such as, for instance, treatment by a concentrated ammonia solution; due to the opening of the lactone rings in basic conditions, acidification to pH below pH 3 to remove excess of ammonia and keep the lactone rings closed should follow. In some cases, it is not necessary to carry out this step as a separate step, since the desired cleavage may have taken place under the operating conditions of the third step: when the deoxygenation is carried out with a trace of 4-(dimethylamino)pyridine (DMAP), deprotected ginkgolide B is obtained directly without the need of performing the deprotection step.

The following examples illustrate the different steps of the process of the invention.

EXAMPLE 1

Step 1: Preparation of C-10 Alkyl Ester of Ginkgolide C

The example as described below give the preparation of C-10 acetate of ginkgolide C. The other alkyl esters will be obtained in the same conditions.

4.40 g (10 mM) of ginkgolide C was dissolved in 20 ml of dimethylformamide (DMF) in a 250 ml round bottom flask. 3.77 ml (40 mM) of acetic anhydride was added and the mixture was stirred overnight (16 hours) at room temperature. The completion of the reaction was checked by HPLC. 10 ml of ethanol was then added and the mixture was evaporated to near dryness under reduced pressure (<25 mmHg, <3333 pascals) on a rotary evaporator over a water bath at 50° C. The residual DMF was removed by adding toluene and evaporating off at about 90° C. under reduced pressure. This operation may be repeated several times to ensure that all the DMF has been removed. The residue obtained was dissolved in 20 ml of ethyl acetate and the resultant solution was added dropwise into a beaker containing 100 ml of n-heptane (or n-hexane or petroleum ether) with constant stirring. The acetate precipitated out in flocs which may be filtered off on a sintered glass filter (porosity 4) and dried in a vacuum oven to yield 4.30 g (90%).

The corresponding C-10 butyrate and C-10 valerate have been prepared in the same conditions as described above, but using n-butyric anhydride and n-valeric anhydride respectively instead of acetic anhydride (Yields: 4.44 g of C-10 butyrate (87%) and 4.88 g of C-10 valerate (93%)).

EXAMPLE 2

Step 2: Preparation of C-7 Phenoxythiocarbonyl Ester of C-10 Acetate of Ginkgolide C Wherein the Phenoxy Group is Optionally Substituted by One or Several Halogen Atoms(s).

The example will give the preparation with a non-substituted phenoxy group. The operating conditions are the same for the conversion to phenoxythiocarbonyl ester, the phenoxy being substituted by one or several halogen atoms.

482 mg (1 mM) of C-10 acetate of ginkgolide C and 490 mg (4 mM) of 4-dimethylaminopyridine (DMAP) was dissolved in 9.6 ml of acetonitrile. Thereafter 276.6 μl (2 mM) of phenylchlorothionocarbonate was added and the mixture was stirred for 20 minutes. The completion of the reaction was checked by HPLC. 20 ml of toluene was then added and the solution was filtered through 10 g of silica gel (Merck 7734). This operation removed DMAP which was absorbed on the silica gel. 20 ml of toluene/acetonitrile (7/3) was added for elution. The filtrate was evaporated off to near dryness and 40 ml of n-hexane (or n-heptane or petroleum ether) were added to precipitate out the product. The precipitate was filtered off on a G4 sintered glass filter and dried in a vacuum oven at ambient temperature to yield 405 mg (66%).

The corresponding C-7 2,4,6-trichloro- and pentafluoro-phenoxythiocarbonyl esters of C-10 acetate of ginkgolide C has been prepared in the same conditions as described above, but using 2,4,6-trichlorophenylchlorothionoformate and pentafluorophenylchlorothionoformate respectively instead of phenylchlorothionocarbonate (Yields: 512 mg (71%) and 475 mg (67%) respectively).

EXAMPLE 3

Step 2: Preparation of C-7 Phenoxythiocarbonyl Ester of C-10 Acetate of Ginkgolide C (Alternative method)

1446 mg (3 mM) of C-10 acetate of ginkgolide C was dissolved in 6 ml of pyridine:chloroform (8:2 by volume). 0.83 ml (2 equivalents) of phenylchlorothionocarbonate was added, and the mixture was stirred (or submitted to ultrasonics) until the yellow precipitate had dissolved. The solution was allowed to stand at ambient temperature until TLC showed no trace of ginkgolide C acetate (2 to 16 hours). 18 ml of toluene was then added to the reaction mixture, and the solution was filtered through a bed of 10 g of silica gel. The product was eluted with 100 ml of toluene:acetone (7:3 by volume). This removed the red colouration from the product. The filtrate was evaporated to near dryness and the viscous liquid was redissolved in 5 to 10 ml of toluene. This solution was added dropwise under stirring to 100 ml of n-hexane, resulting in buff coloured precipitate in flocs. The product was filtered off, washed with 10 ml of n-hexane and dried under reduced pressure at ambient temperature to yield 1.07 of an off-white product (58%).

EXAMPLE 4

Step 2: Preparation of C-7 Imidazolylthiocarbonyl Ester of C-10 Valerate of Ginkgolide C 524 mg (1 mM) of C-10 valerate of ginkgolide C and 244 mg (2 mM) of 4-dimethylaminopyridine (DMAP) were dissolved in 10 ml of acetonitrile. Thereafter 356 mg (2 mM) of 1,1'-thiocarbonyldiimidazole was added and the mixture was stirred for 2 hours at room temperature. The completion of the reaction was checked by HPLC. 15 ml of toluene was then added and the solution was filtered through 10 g of silica gel (Merck 7734). This operation removed DMAP which was absorbed on the silica gel. 25 ml of toluene/acetonitrile (7/3) was added for elution. The filtrate was evaporated off to near dryness and 45 ml of n-hexane (or n-heptane or petroleum ether) were added to precipitate out the product. The precipitate was filtered off on a G4 sintered glass filter and dried in a vacuum oven at ambient temperature to yield 457 mg (72%).

EXAMPLE 5

Step 3: Reaction of C-7, 2,4,6-trichlorophenoxythiocarbonyl Ester of C-10 acetate of ginkgolide C, with Tributyltin Hydride In a 100 ml crimp vial with Teflon-lined septum aluminium cap was dissolved 360 mg (0.5 mM) of C-7 2,4,6-trichlorophenoxythiocarbonyl ester of C-10 acetate of ginkgolide C and 2.5 mg of α,α'-azoisobutyronitrile (AIBN) in 35 ml of acetonitrile. The solution was flushed with argon and 0.54 ml (2 mM) of tributyltin hydride was added. The vial was crimped and warmed to 75° C. for 4 hours in an oil bath. The mixture was analysed by HPLC; 191 mg of C-10 acetate of ginkgolide B was recovered (yield 82%).

EXAMPLE 6

Step 3: Reaction of C-7 imidazolythiocarbonyl ester of C-10 Valerate of Ginkgolide C, with Tris(Trimethylsilyl)Silane The reaction is carried out in the same conditions as described in example 5, by reacting C-7 imidazolylthiocarbonyl ester of C-10 valerate of ginkgolide C (191 mg-0.3 mM) with tris(trimethylsilyl)silane instead of tributyltin hydride. 119 mg of C-10 valerate of ginkgolide B was recovered (yield 78%).

EXAMPLE 7

Step 4: Deprotection Reaction of C-10 Acetate of ginkgolide B

A drop of 30% ammonia solution was added into the reaction mixture as obtained in the example 5. After acidification until pH 3 with hydrochloric acid, 130 mg of ginkgolide B was recovered (yield 77%).

I claim:

1. Process for the preparation of ginkgolide B, of the formula B

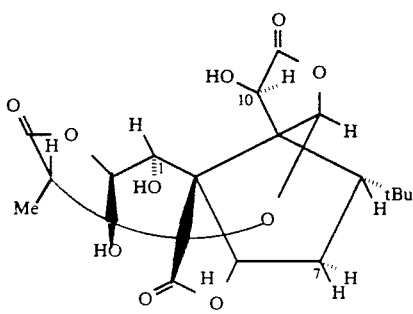

from ginkgolide C, of the formula C

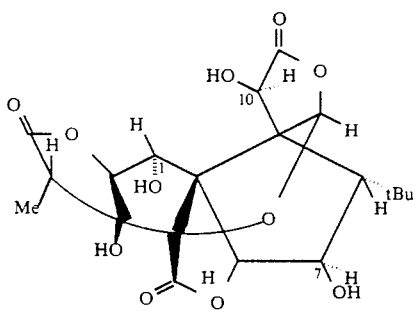

the process comprising the following succession of four steps:

protecting the 10-hydroxy group of ginkgolide C by conversion to an alkyl ester, the reaction being effected in dimethylformamide at a temperature of from 15° to 50° C. for from 4 to 10 hours;

activating the 7-hydroxy group of the resultant 10-protected ginkgolide C by conversion to a (R)thiocarbonyl ester wherein R represents a phenoxy group, a phenoxy group substituted by one or several halogen atom(s), or the imidazolyl group, by treating it respectively with an activating agent selected from within a phenylthiocarbonate, the phenyl group being optionally substituted by one or several halogen atoms(s), and 1,1'-thiocarbonyldiimidazole, the activation being effected in basic conditions at a temperature of from 0° to 40° C. for from 1 to 24 hours;

deoxygenating the 7-activated group in the resultant 10-protected 7-activated ginkgolide C by treating it with tributyltin hydride, in an aprotic solvent, in the presence of a free-radical generator, the reaction being effected at a temperature of from 70° to 110° C. for from 15 minutes to 3 hours under inert atmosphere thereby obtaining 10-protected ginkgolide B; and cleaving the protecting group in the presence of concentrated ammonia solution for removing the 10-hydroxy group from the hereabove 10-protected ginkgolide B.

2. Process according to claim 1 wherein the C-10 hydroxy group is protected as an acetyl, n-butyryl or n-valeryl ester and the protecting agent for such conversion being respectively acetic anhydride, n-butyric anhydride and valeric anhydride.

3. Process according to claim 1 wherein the first step is effected at a temperature of from 20° to 40° C. for from 7 to 9 hours.

4. Process according to claim 1 wherein the 7-hydroxy group of ginkgolide C is converted to a (R)thiocarbonyl ester wherein R represents the phenoxy, 2,4,6-trichlorophenoxy, pentafluorophenoxy or imidazolyl group, by treating it with 1 to 3 equivalents of an activating agent selected from within phenylchlorothionoformate, 2,4,6-trichlorophenylchlorothionoformate, pentafluorophenylchlorothionoformate and 1,1'-thiocarbonyldiimidazole respectively.

5. Process according to claim 1 wherein the second step is effected in solvents mixture containing at least pyridine (1 to 90% by volume) or in acetonitrile containing 2 to 4 equivalents of 4-(dimethylamino)pyridine.

6. Process according to claim 1 wherein the third step is effected in solvents selected from within acetonitrile, benzene, toluene and mixtures thereof.

7. Process according to claim 1 wherein 2 to 4 equivalents of tributyltin hydride or tris-(trimethylsilyl)silane are used in presence of a free-radical generator selected from within α,α'-azo-isobutyronitrile and ter-butylhydroperoxide.

8. Process according to claim 7 wherein the inert atmosphere consists of nitrogen or argon atmosphere.

9. Process according to claim 1 wherein the cleavage of the 10-protecting group in the presence of concentrated ammonia solution is followed by acidification to keep the lactone rings closed.

* * * * *